US012558156B2

(12) United States Patent
O'Halloran et al.

(10) Patent No.: US 12,558,156 B2
(45) Date of Patent: Feb. 24, 2026

(54) SYSTEM COMPRISING AN ELONGATED CATHETER AND AN IMPLANT DETACHABLY ATTACHED TO A DISTAL END OF THE ELONGATED CATHETER

(71) Applicant: AURIGEN MEDICAL LIMITED, Galway (IE)

(72) Inventors: Tony O'Halloran, Turloughmore (IE); John Thompson, Dublin (IE); Shane Regan, Loughrea (IE); Kevin Donaghey, An Spideal (IE); John Kelly, Salthill (IE); Conor Allen, Cappagh Road (IE)

(73) Assignee: AURIGEN MEDICAL LIMITED, Galway (IE)

( * ) Notice: Subject to any disclaimer, the term of this patent is extended or adjusted under 35 U.S.C. 154(b) by 708 days.

(21) Appl. No.: 17/863,257

(22) Filed: Jul. 12, 2022

(65) Prior Publication Data

US 2023/0018512 A1     Jan. 19, 2023

(30) Foreign Application Priority Data

Jul. 13, 2021     (EP) ..................................... 21185454

(51) Int. Cl.
| | |
|---|---|
| *A61B 18/14* | (2006.01) |
| *A61B 17/12* | (2006.01) |
| *A61B 18/00* | (2006.01) |

(52) U.S. Cl.
CPC ...................... *A61B 18/1492* (2013.01); *A61B 2017/12095* (2013.01); *A61B 17/12122* (2013.01);
(Continued)

(58) Field of Classification Search
CPC ........ A61B 17/12122; A61B 17/12172; A61B 17/12177; A61B 2017/00026;
(Continued)

(56) References Cited

U.S. PATENT DOCUMENTS

| | | | |
|---|---|---|---|
| 4,909,789 A | 3/1990 | Taguchi et al. | |
| 5,573,530 A | 11/1996 | Fleury et al. | |
| (Continued) | | | |

FOREIGN PATENT DOCUMENTS

| | | |
|---|---|---|
| EP | 3399933 B1 | 9/2021 |
| WO | 200187168 A1 | 11/2001 |
| (Continued) | | |

OTHER PUBLICATIONS

EPO Search Report issued in European Patent Application No. 21185454.2, dated Jan. 18, 2022.

*Primary Examiner* — Khadijeh A Vahdat
(74) *Attorney, Agent, or Firm* — Bookoff McAndrews, PLLC

(57)     ABSTRACT

A system including an elongated catheter and an implant. The elongated catheter includes a proximal end configured for operative coupling to an electrical supply module, a distal end with a first electrical connector and a first conducting wire to electrically couple the electrical supply module with the first electrical connector. The implant includes a proximal connecting hub configured to detachably mount to the distal end of the elongated catheter, a second electrical connector configured to mate with the first electrical connector, and an active module electrically coupled to the second electrical connector. The first electrical connector is rotatably mounted to the distal end of the elongated catheter and the second electrical connector is non-rotatably attached to the proximal connecting hub of the implant and the elongated catheter can detach from the implant without rotation of the first electrical connector relative to the second electrical connector.

14 Claims, 7 Drawing Sheets

(52) U.S. Cl.
     CPC .............. *A61B 2018/00178* (2013.01); *A61B*
              *2018/00357* (2013.01); *A61B 2018/00577*
                                              (2013.01)

(58) Field of Classification Search
     CPC ........... A61B 2017/00243; A61B 2017/00893;
              A61B 2017/12054; A61B 2017/12095;
          A61B 18/1492; A61B 2018/00172; A61B
              2018/00178; A61B 2018/00357; A61B
                      2018/00577; A61B 2018/1467
     See application file for complete search history.

(56)                References Cited

U.S. PATENT DOCUMENTS

| | | | |
|---|---|---|---|
| 6,454,775 | B1 | 9/2002 | Demarais et al. |
| 6,652,548 | B2 | 11/2003 | Evans et al. |
| 7,655,016 | B2 | 2/2010 | Demarais et al. |
| 10,709,891 | B2 | 7/2020 | Viswanathan et al. |
| 10,842,561 | B2 | 11/2020 | Viswanathan et al. |
| 11,357,978 | B2 | 6/2022 | Bowers et al. |
| 2006/0136034 | A1* | 6/2006 | Modesitt ................... A61F 2/88 |
| | | | 623/1.11 |
| 2010/0286467 | A1* | 11/2010 | Pesach .................. A61M 5/158 |
| | | | 604/257 |
| 2020/0008870 | A1 | 1/2020 | Gruba et al. |
| 2020/0121324 | A1 | 4/2020 | O'Halloran et al. |

FOREIGN PATENT DOCUMENTS

| | | |
|---|---|---|
| WO | 2013109756 A2 | 7/2013 |
| WO | 2018185255 A1 | 10/2018 |
| WO | 2018185256 A1 | 10/2018 |
| WO | 2019157359 A1 | 8/2019 |
| WO | 2020074738 A1 | 4/2020 |
| WO | 2020/163507 A1 | 8/2020 |

* cited by examiner

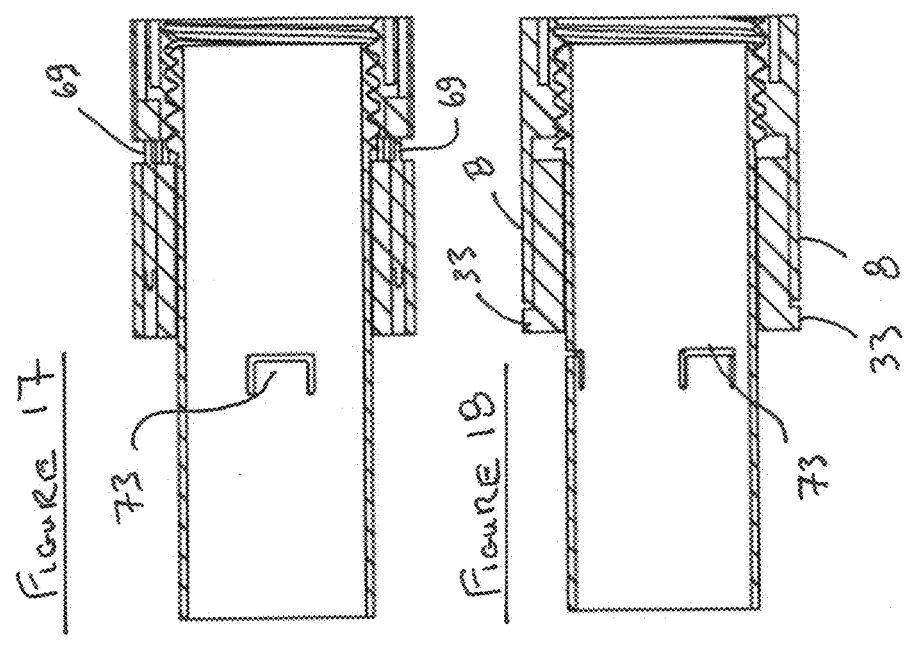
Figure 17
Figure 18
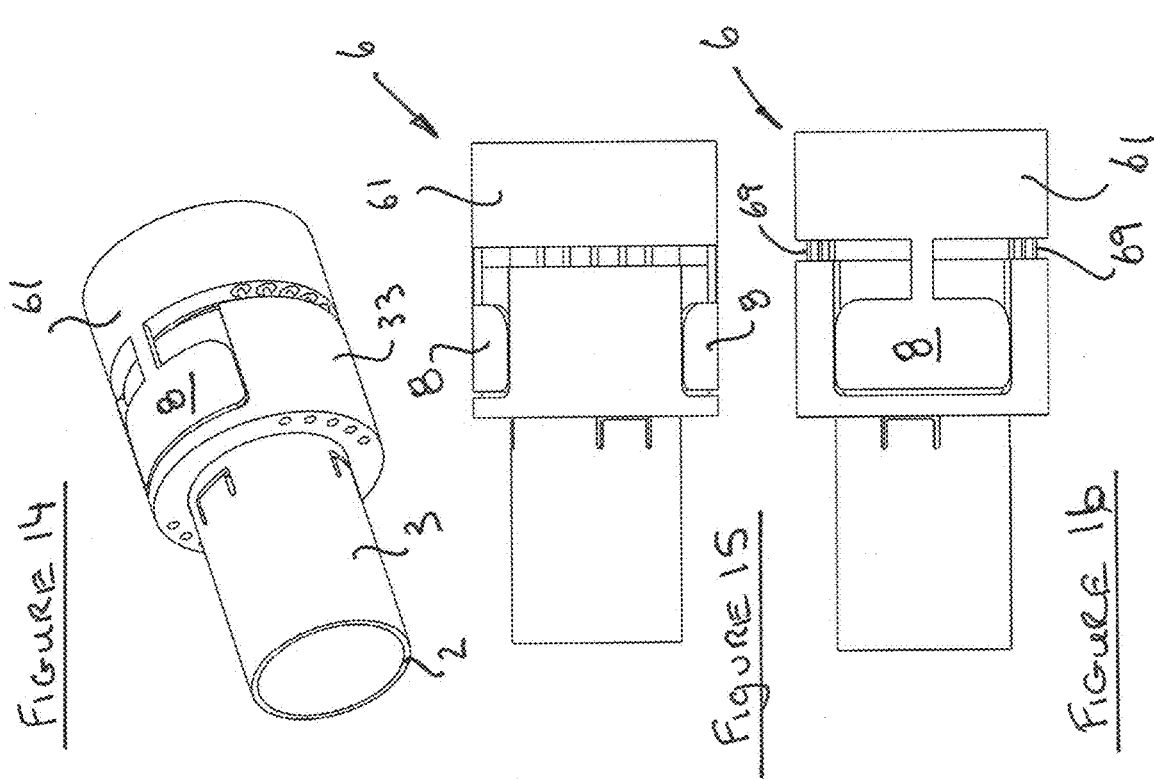
Figure 14
Figure 15
Figure 16

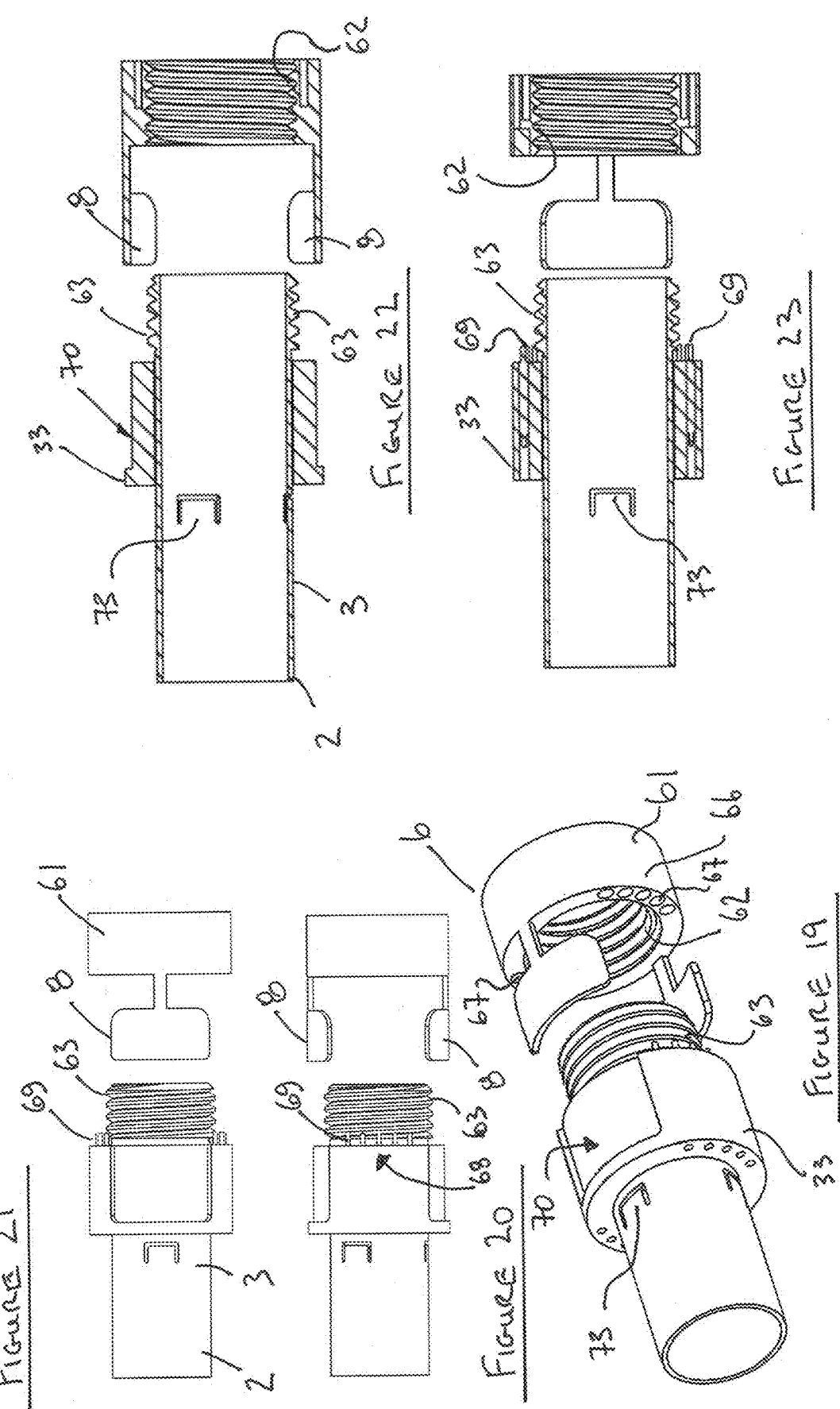

SYSTEM COMPRISING AN ELONGATED CATHETER AND AN IMPLANT DETACHABLY ATTACHED TO A DISTAL END OF THE ELONGATED CATHETER

CROSS REFERENCE TO RELATED APPLICATION

This application claims priority from European Patent Application 21185454.2, filed on Jul. 13, 2021, the entire contents of which being incorporated herein by reference.

TECHNICAL FIELD

The present invention relates to a system comprising an elongated catheter and an implant detachably attached to a distal end of the elongated catheter.

BACKGROUND

Catheter systems comprising elongated catheters and an implant detachably attached to a distal end of the elongated catheter are described in the literature—see for example WO2018185256, WO2018185255 and WO2020074738 in which the implant is an occlusion device for occluding a body lumen such as the left atrial appendage, and in which the catheter is employed to deliver the implant percutaneously to a target site, the implant is deployed and then released from the catheter. The implants often include electrically active modules, for example tissue ablation electrodes or sensors, that require an electrical supply, and in most cases the catheter is configured for electrically coupling the electrode or sensor with an external power supply. This requires that the distal end of the catheter can electrically connect to the implant. Providing electrical connectors on a catheter and implant that are configured to electrically couple and decouple when the catheter and implant couple and decouple is straightforward when the engagement is provided by axial movement of one relative to the other. However, to provide secure engagement between a catheter and implant, threaded engagement is required. In addition, as the electrical connectors have to be insulated from body fluids (such as blood when the system is used in the vasculature), the electrical connectors are generally provided by a pin and socket arrangement which necessitates that the connectors engage in an axial direction. This is problematic when the catheter and implant are configured for threaded engagement.

It is an objective of the invention to overcome at least one of the above-referenced problems.

SUMMARY

The objective is met by the provision of a catheter with a distal end comprising a first electrical connector (with e.g. one of pins or sockets), and an implant with a proximal end comprising a second electrical connector (with e.g. another of pins or sockets), in which the first electrical connector is rotatably mounted to the distal end of the catheter and the second electrical connector is non-rotatably mounted to the implant. This allows the catheter to be rotated (about a longitudinal axis of the catheter) relative to the implant to detach the catheter from the implant without any rotational movement of the first electrical connector relative to the second electrical connector. Rotation of the catheter relative to the implant (unscrewing) results in axial movement of the catheter away from the implant to decouple the first and electrical connectors by axial movement of one relative to the other.

In a first aspect, there is provided a system comprising:

an elongated catheter comprising a proximal end configured for operative coupling to an electrical power source, a distal end with a first electrical connector and a first conducting wire to electrically couple the electrical power source with the first electrical connector; and an implant having a proximal connecting hub configured to detachably mount to the distal end of the elongated catheter by rotation of the elongated catheter relative to the proximal connecting hub, a second electrical connector configured to mate with the first electrical connector, and a tissue energising module electrically coupled to the second electrical connector through a second conducting wire.

Typically, the first electrical connector is rotatably mounted to the distal end of the elongated catheter for rotation about a longitudinal axis of the elongated catheter and the second electrical connector is non-rotatably attached to the proximal connecting hub of the implant such that the elongated catheter can be rotated relative to the implant to detach the elongated catheter from the implant without rotation of the first electrical connector relative to the second electrical connector.

In any embodiment, one of the first or second electrical connectors comprises one or more electrical pins and another of the first or second electrical connectors comprises one or more electrical sockets. Provision of a pin and socket electrical connection electrically insulates the connector to prevent the system shorting when in a liquid environment such as the vasculature.

In any embodiment, the elongated catheter comprises a plurality of first conducting wires electrically connected to the first electrical connector, and the tissue energising module comprises a plurality of electrodes each connected to the second electrical connector by a dedicated second conducting wire, wherein the first and second electrical connectors are configured to mate to electrically couple each first conducting wire with a corresponding second conducting wire. In this manner, the implant may have a number of tissue ablation electrodes, each of which has its own power supply allowing the electrodes to be actuated independently. For example, the elongated catheter may comprise at least four, six, eight or ten first conducting wires electrically connected to the first electrical connector, and the tissue energising module may comprise corresponding electrodes each connected to the second electrical connector by a dedicated second conducting wire.

In any embodiment, the or each first conducting wire is wound around the distal end of the elongated catheter such that when the elongated catheter is rotated relative to the proximal hub, the or each first conducting wire unwinds from the distal end of the elongated catheter. This arrangement allows rotational movement of the catheter relative to the first electrical connector during detachment of the catheter from the implant.

In any embodiment, the tissue energising module comprises tissue ablation electrodes. In any embodiment, the tissue energising module comprises sensing electrodes.

In any embodiment, the implant is a radially expansible occlusion apparatus for occluding a body lumen and is adjustable between a contracted orientation suitable for transluminal delivery and a deployed orientation configured to occlude the body lumen.

In any embodiment, the implant is a radially expansible occlusion apparatus for occluding a left atrial appendage of the heart.

In any embodiment, the radially expansible occlusion apparatus comprises:

a cylindrical cage body having a sidewall, an optionally open distal end and a concave proximal end wall with a raised connecting hub with an open proximal end typically providing a through lumen into the cylindrical cage body; and a cover proximal of the raised connecting hub having a closable aperture providing access to the raised connecting hub from a proximal side of the occlusion apparatus.

In any embodiment, the distal end of the elongated catheter and the proximal hub of the implant are threaded to provide threaded engagement between the elongated catheter and the implant.

In any embodiment, the distal end of the elongated catheter is externally threaded and the proximal hub of the implant comprises a cylindrical annulus that is internally threaded and configured to receive the externally threaded distal end.

In any embodiment, the proximal connecting hub of the implant comprises an open proximal end defined by an annular sidewall and two wing elements mounted on opposed sides of the annular sidewall that are configured for movement from an at rest closed configuration in which the wing elements are folded over the open proximal end of the raised connecting hub to an open tensioned configuration in which the wing elements extend proximally annular sidewall.

In any embodiment, the second electrical connector is attached to one of the wing elements.

In any embodiment, the implant comprises a second electrical connector attached to each of the wing elements.

Embodiments having second electrical connectors attached to one or both of the wing elements are best illustrated in FIGS. 6 to 11.

In another embodiment, the second electrical connectors are disposed on the annular sidewall. This is illustrated in FIGS. 14 to 20. In any embodiment, the second electrical connector comprises one second electrical connector part disposed on one side of the annular sidewall (generally circumferentially spaced apart from the wings) and another second electrical connector part disposed on an opposite side of the annular sidewall (generally circumferentially spaced apart from the wings). Generally, in this embodiment, the second electrical connector comprises one or more electrical pin receiving sockets.

In any embodiment, the first electrical connector and wing elements of the proximal connecting hub are dimensioned to next together when the distal end of the catheter and proximal connecting hub are connected together.

In any embodiment, a radially outer wall of the first electrical connector comprises surface recesses configured to receive the wing elements of the proximal connecting hub in a nested configuration when the distal end of the catheter and proximal connecting hub are connected together. This is best illustrated in FIGS. 19 to 21.

In any embodiment, the wings are typically connected to the blood impermeable cover on each side of the aperture whereby when the wings are in the closed configuration the aperture in the blood impermeable cover is closed to prevent movement of blood through the raised connecting hub.

In any embodiment, the wings are formed from a shape memory material and are biased into the closed configuration.

In any embodiment, the cover comprises a first cover part attached to one wing and a second part attached to a second wing.

In any embodiment, the first and second cover parts are semi-circular.

In any embodiment, the two parts are configured to at least partially overlap when the wings are in the closed configuration.

In any embodiment, one of the first electrical connector and second electrical connector comprises a housing with one or more electrical sockets (female connector) and another of the first electrical connector and second electrical connector comprises a housing with one or more electrical pins (male connector) corresponding to the one or more electrical sockets.

In any embodiment, the second electrical connector comprises a housing with one or more electrical sockets and the first electrical connector comprises a housing with one or more electrical pins corresponding to the one or more electrical sockets.

In any embodiment, the male electrical connector comprises a resiliently deformable sidewall part in which the or each electrical pin projects proud of the resiliently deformable sidewall part. The provision of a resiliently deformable sidewall part around the pins allows the electrical connectors tightly abut and fluidically isolate the pins and sockets.

In any embodiment, the first electrical connector comprises an annular housing rotatably mounted to the distal end of the elongated catheter having a radially inner wall, a radially outer wall, and distal and proximal sidewalls.

In any embodiment, the distal sidewall comprises one or more electrical pins or electrical sockets arranged coaxially with a longitudinal axis of the elongated catheter.

In any embodiment, the distal end of the catheter comprises a stop element configured to prevent axial proximal movement of the first electrical connector along the distal end of the catheter.

In any embodiment, the distal end of the catheter comprises a plurality of stop elements circumferentially spaced around the distal end of the catheter.

In any embodiment, the or each stop element comprises a spring, typically a leaf spring. The leaf spring may be formed from a cut-out section of the distal end of the catheter as illustrated in FIGS. 14 to 16.

In any embodiment, the system comprises an electrical controller coupled to an electrical power source and the or each conducting wire of the catheter and configured to energise the or each active module of the implant when the implant and catheter are electrically coupled.

In another aspect, there is provided a system comprising:

an elongated catheter comprising a proximal end configured for operative coupling to an electrical supply module, a distal end with a first electrical connector and a first conducting wire to electrically couple the electrical supply module with the first electrical connector; and an implant having a proximal connecting hub configured to detachably mount to the distal end of the elongated catheter, a second electrical connector configured to mate with the first electrical connector, and an active module electrically coupled to the second electrical connector through a second conducting wire.

In any embodiment, the first electrical connector comprises a housing having one of an electrical pin or electrical socket and the second electrical connector comprises a housing having another of an electrical pin or electrical socket.

In any embodiment, the housing of the electrical connector comprising the electrical pin (male electrical connector) comprises a resiliently deformable sidewall part in which the or each electrical pin projects proud of the resiliently deformable sidewall part.

In another aspect, there is provided a method comprising the steps of providing a system according to any embodiment of the disclosure with the proximal hub of the implant connected to the distal end of the catheter and first electrical connector electrically coupled to the second electrical connector;

advancing the catheter and implant transluminally to a target site in a body lumen;

electrically energising the or each active module of the implant;

rotating the elongated catheter relative to the implant to detach the catheter from the implant and decouple the first electrical connector from the second electrical connector without rotation of the first electrical connector relative to the second electrical connector; and withdrawing the elongated catheter transluminally to leave the implant in-situ.

In any embodiment, the method is a method of ablating tissue of the body lumen, in which the or each active module is a tissue energising module.

Other aspects and preferred embodiments of the invention are defined and described in the other claims set out below.

6 the first conducting wires are shown coiled around the catheter proximal of the first electrical connector.

Figure 9:
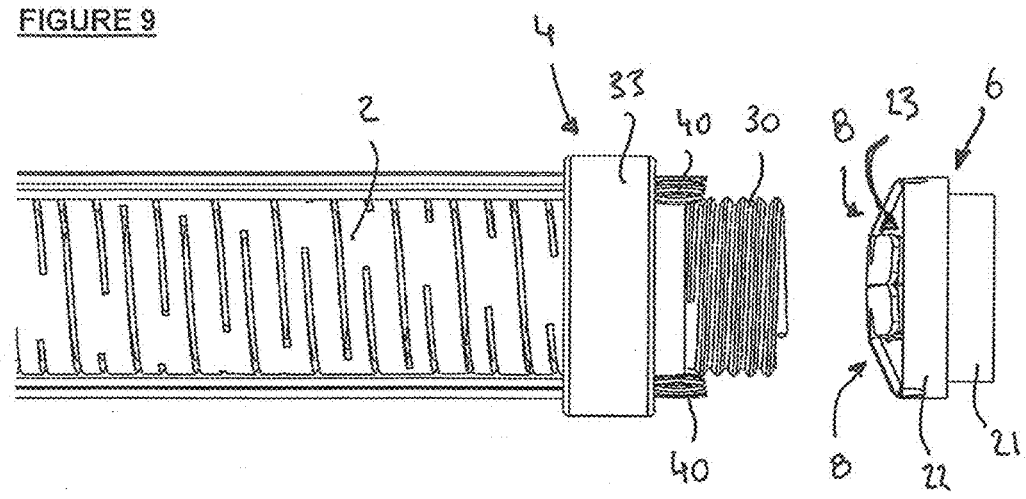

FIG. 9 is a side elevational view of the distal end of the elongated catheter detached from the proximal connecting hub of the implantable occlusion apparatus and the second electrical connectors decoupled to the first connector, with the wing elements in a closed configuration covering the open proximal end of the connecting hub.

Figure 10:
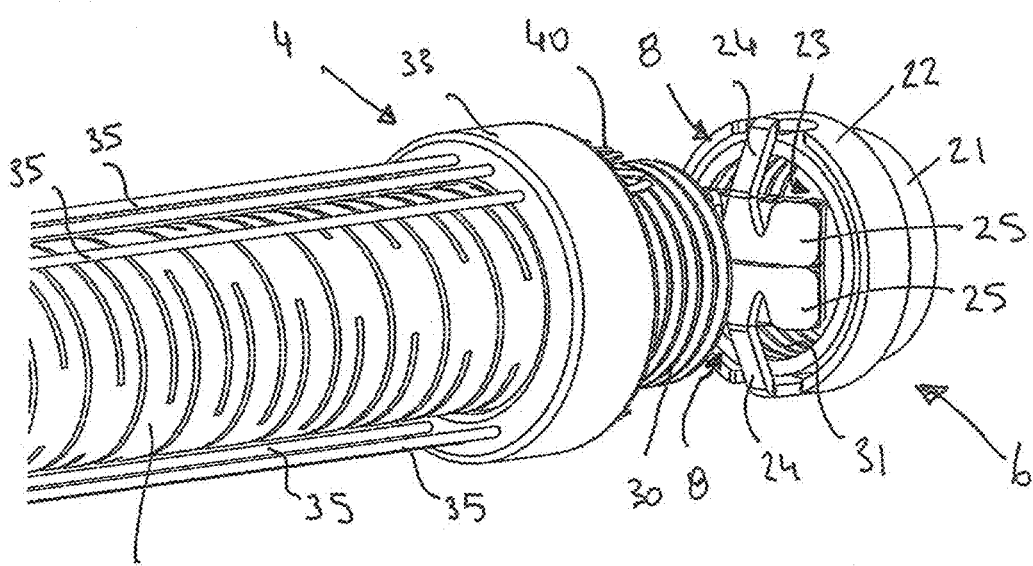

FIG. 10 is a perspective view of the distal end of the elongated catheter detached from the proximal connecting hub of the implantable occlusion apparatus and the second electrical connectors decoupled to the first connector, with the wing elements in a closed configuration covering the open proximal end of the connecting hub.

Figure 11:
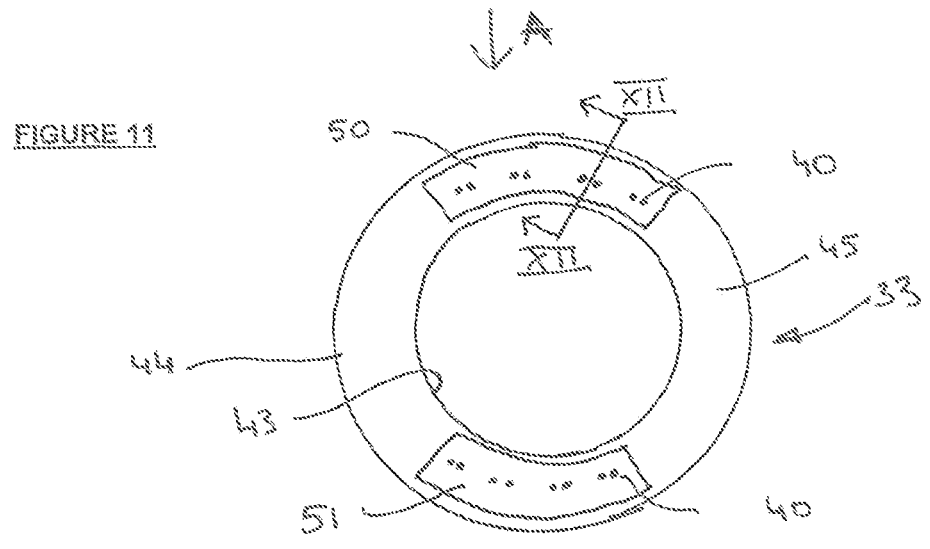

FIG. 11 is an elevational view of the first electrical connector looking towards a distal sidewall of the annular ring.

Figure 12:
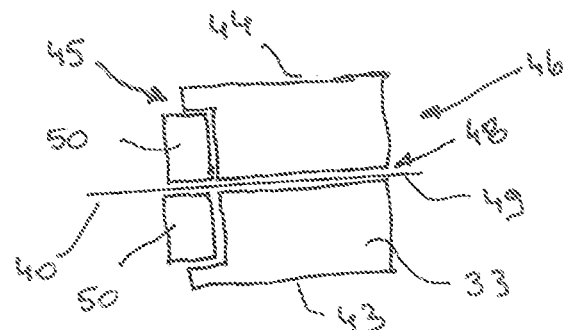

FIG. 12 is a sectional view taken along the lines XII-XII of FIG. 11.

Figure 13:
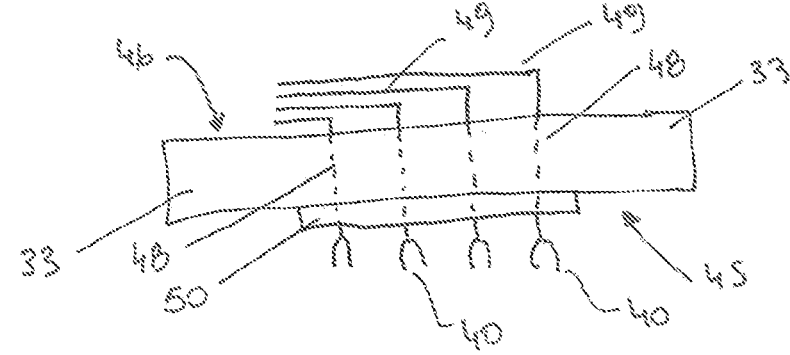

FIG. 13 is a top plan view of the first electrical connector looking in a direction of the arrow A in FIG. 11.

FIG. 14 is a perspective view of an alternative connection system for an implantable occlusion device according to the invention, showing in a connected configuration.

FIG. 15 is a side elevational view of the connection system of FIG. 14.

FIG. 16 is a top elevational view of the connection system of FIG. 14.

FIG. 17 is a sectional view of the connection system of FIG. 16.

FIG. 18 is a sectional view of the connection system of FIG. 15

FIG. 19 is a perspective view of the alternative connection system of FIG. 14, shown in a disconnected configuration.

FIG. 20 is a top elevational view of the connection system shown in FIG. 19.

FIG. 21 is a side elevational view of the connection system shown in FIG. 19.

FIG. 22 is a sectional view of the connection system shown in FIG. 20.

FIG. 23 is a sectional view of the connection system shown in FIG. 21.

DETAILED DESCRIPTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, age, poisoning or nutritional deficiencies.

As used herein, the term "treatment" or "treating" refers to an intervention (e.g. the administration of a PFA treatment to a subject) which cures, ameliorates or lessens the symptoms of a disease or removes (or lessens the impact of) its cause(s). In this case, the term is used synonymously with the term "therapy".

Additionally, the terms "treatment" or "treating" refers to an intervention (e.g. the administration of a PFA treatment to a subject) which prevents or delays the onset or progression of a disease or reduces (or eradicates) its incidence within a treated population. In this case, the term treatment is used synonymously with the term "prophylaxis".

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, camels, bison, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human. As used herein, the term "equine" refers to mammals of the family Equidae, which includes horses, donkeys, assess, kiang and zebra.

"Implantable occlusion apparatus" means an apparatus configured for implantation in a body lumen, especially implantation in the heart at least partially or fully within the left atrial appendage, and upon actuation to at least partially or fully fluidically occlude the body lumen. The occlusion apparatus is typically detachably connected to a delivery catheter which delivers the occlusion apparatus to the target site, and typically remains attached during occlusion, sensing and energy delivery treatments and in one embodiment is generally detached after the energy delivery treatment and removed from the body leaving the occlusion apparatus implanted in the body lumen. Occlusion may be complete occlusion (closing) of the body lumen or partial occlusion (narrowing of the body lumen or near complete occlusion). The occlusion apparatus typically comprises a body that is expansible from a contracted delivery configuration to an expanded deployed configuration. The body may take many forms, for example a wireframe structure formed from a braided or meshed material. Examples of expandable wireframe structures suitable for transluminal delivery are known in the literature and described in, for example, WO01/87168, U.S. Pat. No. 6,652,548, US2004/219028, U.S. Pat. Nos. 6,454,775, 4,909,789, 5,573,530, WO2013/

109756. Other forms of bodies suitable for use with the present invention include plate or saucer shaped scaffolds, or stents. In one embodiment, the body is formed from a metal, for example a shape-memory metal such as nitinol. The body may have any shape suitable for the purpose of the invention, for example cylindrical, discoid or spheroid. In one preferred embodiment, the apparatus comprises a cylindrical body, for example a cylindrical cage body. In one embodiment, the body comprises a tissue energising module. In one embodiment, the ablation device comprises an array of electrodes, typically a circumferential array. In one embodiment, the array of electrodes are configured to deliver pulsed field ablation to the tissue. In one embodiment, a distal face of the radially expansible body comprises a covering configured to promote epithelial cell proliferation. In one embodiment, the body comprises a stepped radial force stiffness profile from distal to proximal device. In one embodiment, the body comprises a metal mesh cage scaffold. In one embodiment, a coupling between the body and the catheter member is located distally to the left atrial facing side of the body. In one embodiment, the body in a deployed configuration has a radial diameter at least 10% greater than the radial diameter of the left atrial appendage at a point of deployment. In one embodiment, the furthermost distal part is configured to be atraumatic to cardiac tissue. In one embodiment, the body comprises a braided mesh scaffold that in one embodiment is conducive to collagen infiltration on thermal energy delivery to promote increased anti migration resistance. Examples of an implantable occlusion apparatus for use in a body lumen especially the LAA are described in WO2018/185256, WO2018/185255 and WO2020/074738.

"Body lumen" means a cavity in the body, and may be an elongated cavity such as a vessel (i.e. an artery, vein, lymph vessel, urethra, ureter, sinus, auditory canal, nasal cavity, bronchus) or an annular space in the heart such as the left atrial appendage, left ventricular outflow tract, the aortic valve, the mitral valve, mitral valve continuity, or heart valve or valve opening.

"Detachably attached" means that the device is configured such that the occlusion apparatus is attached to the elongated delivery catheter during delivery and can be released after deployment and treatment whereby the occlusion apparatus is implanted in the heart and the elongated delivery catheter can be withdrawn leaving the occlusion apparatus in-situ. Typically, the device includes a control mechanism for remotely detaching the occlusion apparatus or radially expansible element from the elongated catheter member. Typically, an actuation switch for the control mechanism is disposed on the control handle.

"Transluminal delivery" means delivery of the occlusion apparatus to a target site (for example the heart) heart through a body lumen, for example delivery through an artery or vein. In one embodiment, the device of the invention is advanced through an artery or vein to deliver the occlusion apparatus to the left atrium of the heart and at least partially in the LAA. In one embodiment, the device is delivered such that the distal part is disposed within the LAA and the proximal part is disposed in the left atrium just outside the LAA. In one embodiment, the device is delivered such that the distal part is disposed within the LAA and the proximal part is disposed in the left atrium abutting a mouth of the LAA. In one embodiment, the device is delivered such that both the distal and proximal parts are disposed within the LAA.

"Cover": Typically, the implantable occlusion apparatus has a proximal cover which is impermeable to blood and that may include a re-closable aperture, for example an overlapping flap of material. The re-closable aperture may be configured to allow a distal end of the catheter through the aperture while preventing blood flow through the aperture. The occlusion apparatus may include a connecting hub distal of the cover and configured for coupling with a distal end of the catheter. The cover may be configured to act as a scaffold for in-vivo endothelialisation. The cover may be formed from a woven mesh material.

"Covering/cover configured to act as a scaffold for in-vivo endothelialisation" means a material that is use promotes epithelialisation of the distal or proximal body. In one embodiment, the covering is a membrane that comprises agents that promote epithelial cell proliferation. Examples include growth factors such as fibroblast growth factor, transforming growth factor, epidermal growth factor and platelet derived growth factor, cells such as endothelial cells or endothelial progenitor cells, and biological material such as tissue or tissue components. Examples of tissue components include endothelial tissue, extracellular matrix, submucosa, dura mater, pericardium, endocardium, serosa, peritoneum, and basement membrane tissue. In one embodiment, the covering is porous. In one embodiment, the covering is a biocompatible scaffold formed from biological material. In one embodiment, the covering is a porous scaffold formed from a biological material such as collagen. In one embodiment, the covering is a lyophilised scaffold.

"Tissue energising module" as used herein refers to one or more electrodes disposed on the implantable occlusion apparatus configured for electrical coupling with an energy supply module via the catheter and electrical connectors. The electrodes are generally individually coupled with the energy supply module to allow electrode specific energising. They array of electrodes is generally arranged on the implantable occlusion apparatus in a circumferential arrangement and configured to contact the wall of the body lumen in a circumferential pattern when the apparatus is deployed. The electrodes are configured to deliver energy, generally PFA, circumferentially around the wall of the body lumen. The electrodes may also function as sensors to detect an electrical parameter of the tissue of the wall of the body lumen, for example electrical impedance or electrical activity (voltage). The electrodes may be configured to measure an electrical parameter radially across the wall of the body lumen, or circumferentially along a section of the circumference of the wall of the body lumen. Generally, measuring an electrical parameter such as electrical impedance radially across the wall of the body lumen employs an electrode of the array of electrodes and an earth or ground pad placed on the patient's body, often the leg. Measuring an electrical parameter such as electrical impedance circumferentially along a section of the body lumen employs two electrodes where one electrode functions as an energising electrode and the other functions as a detecting electrode. The electrical parameter such as electrical impedance may be measured at one frequency or over a range of frequencies.

"Electrical controller" refers to a pulsed field energy delivery generator that comprises or can be operably coupled to an electrical power source and is operatively coupled to the plurality of electrodes and configured to energise the electrodes, typically in a pulsed field ablation modality. In one preferred aspect, the controller comprises a signal generator configured for generating a pulse waveform. In any embodiment, the signal generator is configured to deliver at least one train of PFA energy to an electrode. In any embodiment, the signal generator is configured to deliver a train of energy of at least 20 pulses to an electrode.

In any embodiment, the signal generator is configured to deliver at least one train of energy comprising an inter-phase delay of between 0 μs and 100 μs. In any embodiment, the signal generator is configured to deliver a train of energy comprising an inter-pulse delay of 1 to 100 μs, and typically at least 5 μs. In any embodiment, the signal generator is configured to deliver a train of energy comprising a pulse width of 100 ns-100 μs. In any embodiment, the signal generator is configured to deliver at least one train of PFA energy having a voltage amplitude between 100V and 5000V. In any embodiment, the signal generator is configured to deliver pulses in monophasic or biphasic form. The electrical controller is operably coupled to some or all of the electrodes (or electrode pairs) in the array in a manner allowing electrode pairs to be energised independently. The electrical controller may a comprise a plurality of electrode channels, and optionally a routing channel. Such an electrical controller is described in US2020230403. Electrical controllers for generating pulsed field ablative energy are described in EP3399933, US2020046423, WO2019157359 and US2020139114. Fraczek et al. describes the use of two electrodes or four electrodes to measure electrical impedance in tissue.

"Atrial fibrillation" or "AF" is a common cardiac rhythm disorder affecting an estimated 6 million patients in the United States alone. AF is the second leading cause of stroke in the United States and may account for nearly one-third of strokes in the elderly. In greater than 90% of cases where a blood clot (thrombus) is found in the AF patient, the clot develops in the left atrial appendage (LAA) of the heart. The irregular heartbeat in AF causes blood to pool in the left atrial appendage, because clotting occurs when blood is stagnant, clots or thrombi may form in the LAA. These blood clots may dislodge from the left atrial appendage and may enter the cranial circulation causing a stroke, the coronary circulation causing a myocardial infarction, the peripheral circulation causing limb ischemia, as well as other vascular beds. The term includes all forms of atrial fibrillation, including paroxysmal (intermittent) AF and persistent and longstanding persistent AF (PLPAF).

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Figure 1:
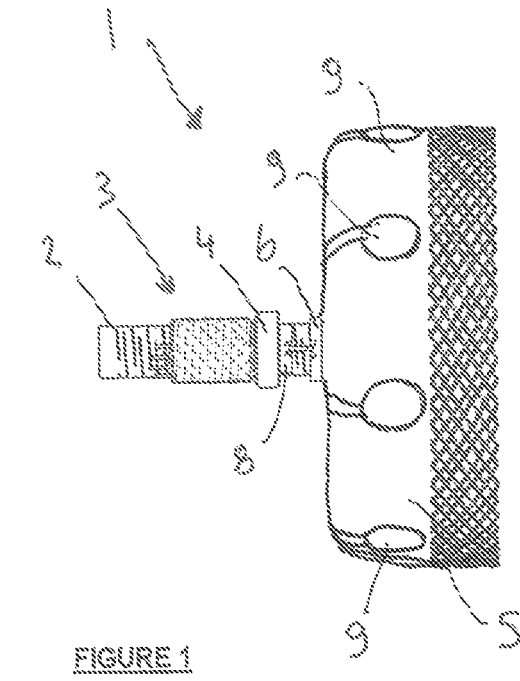
FIG. 1 is a perspective view of an implantable occlusion apparatus forming part of the system of the invention showing the concave proximal end and proximal connection hub.
Figure 2:
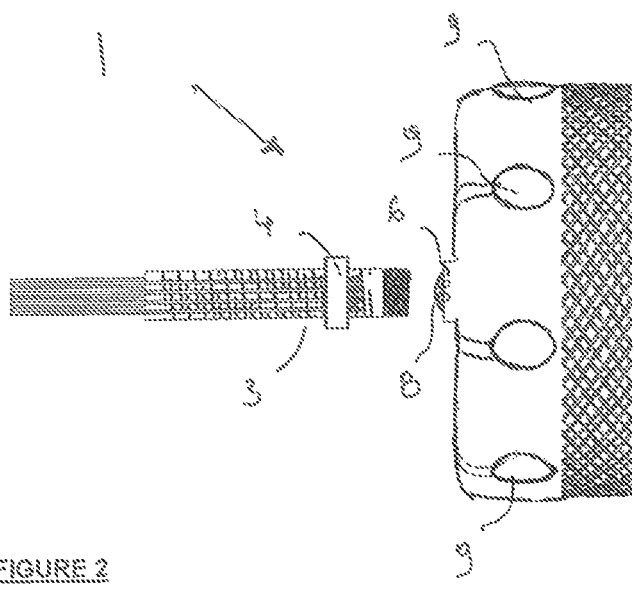
FIG. 2 is a perspective view of an implantable occlusion apparatus forming part of the system of the invention showing the concave proximal end and proximal connection hub.

Referring to the drawings, and initially to FIGS. 1 and 2, there is illustrated a system according to the invention indicated generally by the reference numeral 1 and comprising an elongated catheter 2 having a distal end 3 and first electrical connector 4, and an implant 5 having a proximal connection hub 6, second electrical connectors (not shown) attached to wing elements 8 attached to each side of the proximal connection hub 6, and active modules (in this case tissue ablation electrodes 9) that are electrically connected to the second electrical connectors. In this example, the implant is a radially expansible occlusion apparatus for occlusion of the left atrial appendage (LAA) of the heart that is adjustable between a contracted orientation suitable for transluminal delivery (not shown) and a deployed orientation configured to occlude the LAA (shown). In FIG. 1, the system is shown with the implant 5 attached to the catheter 2. This is how the device is assembled prior to use, and the configuration used to deliver the implant to the LAA. During transluminal delivery the occlusion apparatus is contracted and only deployed once the occlusion apparatus is positioned correctly (which can be confirmed using contrast dye or X-ray imaging). Once in position, the occlusion apparatus is deployed into circumferential contact with the wall of the LAA and the electrodes of the occlusion apparatus may then be energised to perform a tissue ablation treatment or to sense a parameter such as electrical impedance of the tissue. During a treatment or sensing procedure, the electrodes 9 are energised by electrical power supplied by an external energy supply via conducting wires in the catheter and occlusion apparatus.

FIG. 2 illustrates the system after the implant 5 (occlusion apparatus) has been detached from the distal end 3 of the elongated catheter 2. Detachment of the catheter 2 and implant 5 causes decoupling of the first electrical connector 4 and second electrical connectors 7, with the wing elements 8 (not shown in FIG. 2) closed over the proximal connection hub 6. At this point, the implant remains in-situ fluidically isolating the LAA and the elongated catheter may be withdrawn percutaneously.

Figures 3, 4, 5:
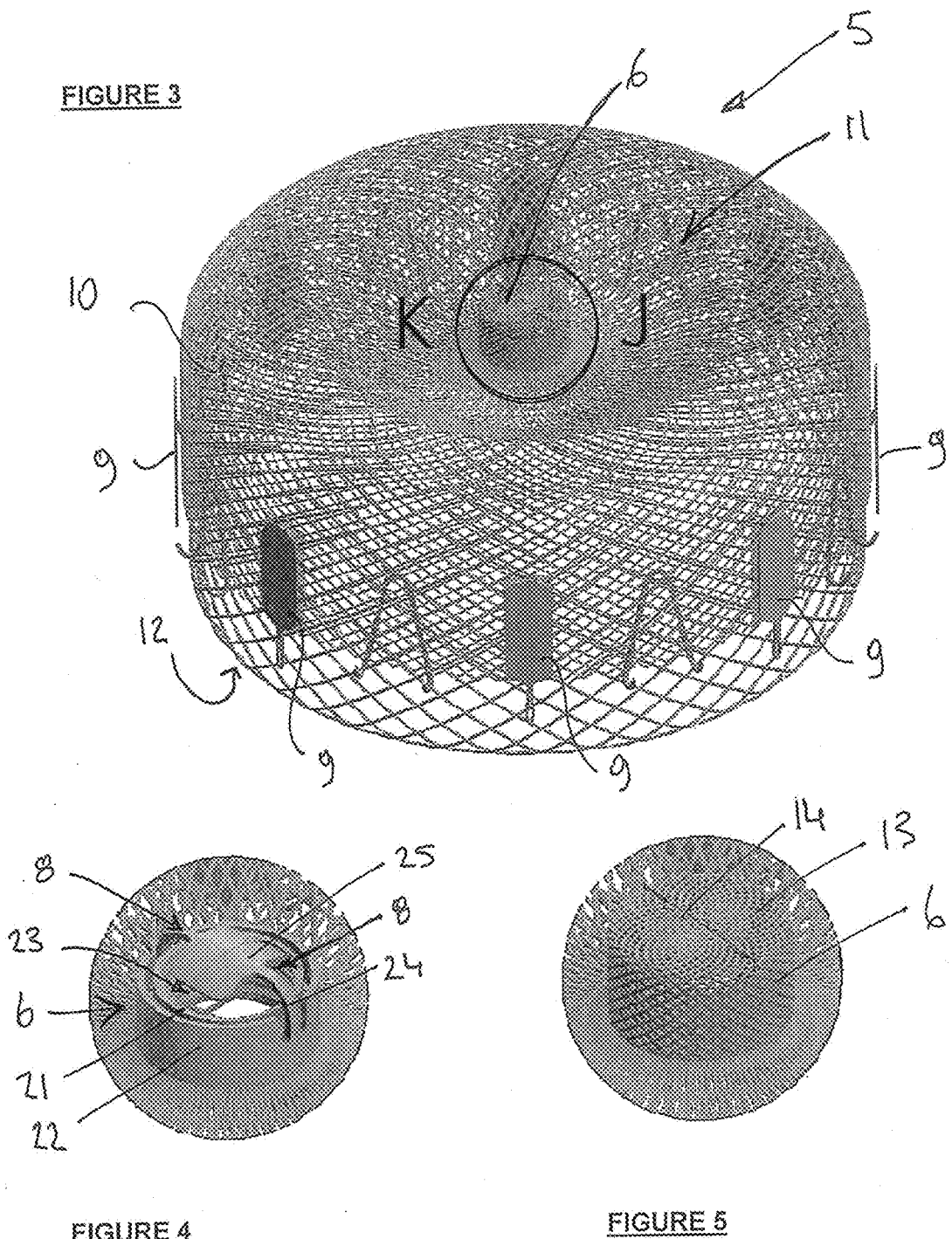
FIG. 3 is a perspective view of an implantable occlusion apparatus forming part of the system of the invention showing the concave proximal end and proximal connection hub.
FIG. 4 is a detailed view of the proximal connecting hub with the cover layer removed to showing the open proximal end and two wing elements mounted on opposed sides of the open proximal end in a closed configuration.
FIG. 5 is a detailed view of the proximal connecting hub with the cover layer shown covering the open proximal end.
Figures 6, 7, 8:
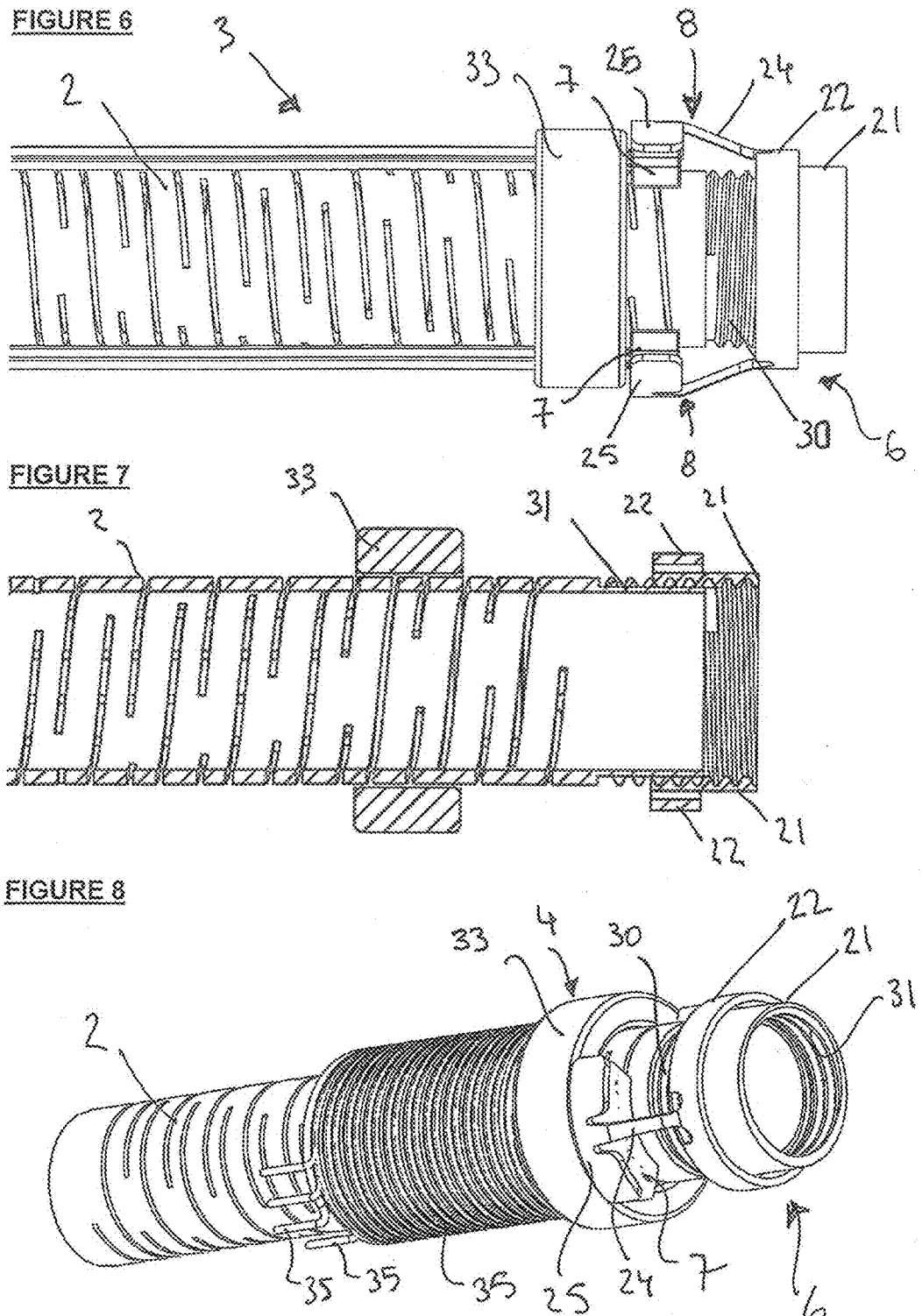
FIG. 6 is a side elevational view of the distal end of the elongated catheter in threaded engagement with the proximal connecting hub of the implantable occlusion apparatus and the second electrical connectors mounted to the wing elements electrically coupled to the annular first connector.
FIG. 7 is a sectional view of the distal end of the elongated catheter in threaded engagement with the proximal connecting hub of the implantable occlusion apparatus with the wing elements removed for clarity.
FIG. 8 is a perspective view of the distal end of the elongated catheter in threaded engagement with the proximal connecting hub of the implantable occlusion apparatus. The second electrical connectors mounted to the wing elements are electrically coupled to the first connector.

Referring to FIGS. 3 to 5, the implantable occlusion apparatus 5 (implant) is shown in more detail, in which parts described with reference to the previous figures are assigned the same reference numerals. The implantable occlusion apparatus 5 comprises a cylindrical mesh cage 10 with a recessed (concave) proximal end 11 and an open distal end 12. The proximal connection hub 6 is provided on the proximal end, distal of a blood-impermeable cover membrane 13 having a slitted aperture 14. An array of eight electrodes 9 are provided circumferentially around the wall of the occlusion apparatus at equally spaced apart locations. Each electrode 9 is connected to the connecting hub 6 with a dedicated insulated lead (not shown). Referring to FIG. 4, the proximal connecting hub 6 is illustrated with the blood-impermeable cover membrane 13 removed for clarity. The hub 6 comprises a cylindrical housing defined by an inner wall 21 that is internally threaded and an external wall 22 and an open proximal end 23. The wing elements 8 are T-shaped and have a stem 24 attached to the external wall 22 and a distal end 25 that is curved, and are configured for adjustment from an at rest closed configuration in which the wing elements are folded over the open proximal end 23 of the connecting hub 6 (FIG. 4) to an open tensioned configuration (FIG. 8). FIG. 5 is the same as FIG. 4 but with the blood impermeable cover membrane 13 shown covering the open proximal end 23 of the hub 6.

FIGS. 6 to 8 show the system in more detail with the implant attached and electrically coupled to the catheter, and FIGS. 9 and 10 show the system with the implant detached and electrically decoupled from the catheter.

Referring initially to FIGS. 6 to 8, the distal end 3 of the catheter 2 is attached to the implant 5 by means of external threads 30 on the catheter 2 that engage internal threads 31 on the inner wall 21 of the connection hub 6. Thus, the implant is screwed on to the end of the catheter prior to use of the system. The first electrical connector 4 is provided by an annular ring 33 that is mounted to the distal end 3 of the catheter 2 for rotation on the catheter about a longitudinal axis of the catheter. This allows the catheter to be rotated relative to the implant to unscrew and detach the catheter from the implant, without having the first electrical connector 4 rotate. This is a key element of the invention, as it allows the catheter to be unscrewed without rotation of the first and second electrical connectors relative to each other. Although not shown, the distal end 3 of the catheter 2 will include annular formations which prevent axial movement of the first electrical connector 4 relative to the catheter 2. This ensures that as the catheter and implant are unscrewed, the axial retraction of the catheter relative to the implant will result in axial retraction of the first electrical connector relative to the second electrical connector to electrically decouple the connectors. FIGS. 6 and 8 show the second electrical connectors 7 attached to the curved distal end 25 of the T-shaped wing elements 8, and electrically coupled to opposite sides of annular ring 33. The details of the first and second electrical connectors are provided in FIGS. 9 and 10. FIG. 8 illustrates conducting wires 35 that provide electrical power from an external power supply to the first electrical connector 4. As the system comprises eight electrodes, the catheter 2 comprises eight conducting wires 35, four of which are electrically connected to one side of the annular ring (for connection with a first of the second electrical connectors 7) and four of which are electrically connected to an opposite side of the annular ring (for connection with a second of the second electrical connectors 7). When the system is assembled prior to use, the conducting wires are wound around the distal end 3 of the catheter 2 proximal of the first electrical connector (annular ring 33) in such a way as to allow the wires unwind when the catheter is rotated relative to the annular ring 33. This is required when the catheter and implant are configured for threaded engagement. In other embodiments, for example when the engagement between the catheter and implant is not threaded (for example it could be a twist and lock engagement), the wires do not need to be wound around the catheter.

FIGS. 9 and 10 illustrate the system with the implant (occlusion apparatus 5) detached from the catheter 2, the wing elements 8 folded over the open proximal end 23 of the proximal connection hub 6 (the blood impermeable cover is left out for clarity), and the electrical pins 40 exposed proud of a distal side of the first electrical connector (annular ring 33). Although not shown, the second electrical connectors 7 include sockets dimensioned to receive the electrical pins 40 of the first electrical connector.

FIGS. 11 to 13 illustrate the first electrical connector 4 in more detail. The connector comprises an annular ring 33 having a radially inner wall 43, radially outer wall 44, and distal sidewall 45 and proximal sidewall 46. The inner diameter of the ring 33 is dimensioned to be slightly larger than the outer diameter of the distal end of the catheter 2 (not shown) to allow rotation thereon without any significant play. The ring 33 is formed of polycarbonate having a series of parallel bores 48 that extends across the ring for accommodating gold electrical conducting wires 49 terminating in electrical pins 40. The distal sidewall 45 has two electrical connection section 50 and 51, formed of a resiliently deformable silicone material that are inserted into corresponding recesses in the sidewall 45 such that a distal part of the silicone material is exposed proud of the distal sidewall 45. This ensures that when the first and second electrical connectors are brought together, the silicone material is compressed against the second connectors fluidically isolating the electrical conducting wires 49 and pins 40.

Referring to FIGS. 14 to 23, a further embodiment of the invention is described in which parts described with reference to previous embodiments are assigned the same reference numerals. In the previously described embodiments, the second electrical connected are mounted to the wings 8 of the connecting hub of the implant. In the embodiment of FIGS. 14 to 23, the second electrical connectors are disposed on the annular sidewall of the hub, as opposed to the wings. The proximal hub 6 of the implant 5 has an annular sidewall

61 having internal threads 62 and the distal end 3 of the catheter 2 has external threads 63 configured to engage the threads 61 of the hub 6. The annular sidewall 61 has a proximal wall 64 configured to abut the distal wall 65 of the distal end 3 of the catheter 2 when the catheter and implant are coupled together. Second electrical connector sections 66 are provided on each side of the proximal wall 64 each comprising five electrical sockets 67, and the distal wall 65 of the rotatable annular ring includes corresponding first electrical connector sections 68 each having five protruding electrical pins 69 configured to electrically couple with the corresponding sockets 67 of the hub 6. The wings 8 in this embodiment are configured to embrace part of the annular ring 33 and nest in recesses 70 formed on opposite sides of the external wall of the annular ring 33 in a tight but sliding relationship. Four leaf springs 73 are formed on an external surface of the distal end of the catheter and function to control and limit movement of the annular ring 33 proximally when the catheter and implant are coupled (screwed) together. The leaf springs are formed by providing a U-shaped cut-out in the wall of the distal end of the catheter to provide a tongue element 74 that projects upwardly proud of a surface of the distal end 3 of the catheter 2. Thus, when the annular ring 33 is urged proximally due to the catheter and implant being screwed together, the free end of the tongue will bear against the annular ring and exert a stopping force which is variable due to the bending of the tongue.

In use, the system is first assembled by opening the wings of the occlusion apparatus and screwing the occlusion apparatus to the distal end of the catheter until they are locked tight. During the threaded coupling of the implant to the catheter, the implant will move axially towards the catheter bringing the second electrical connectors of the occlusion apparatus into contact with the first electrical connector of the catheter, with the pins of the first connector being received in the sockets of the second connectors and in some embodiments the connectors abutting to compress the silicone wall of the first electrical connector against the wall of the second electrical connectors to form a fluidically tight seal around the electrical pins and sockets. The system is then advanced percutaneously to a target location in a body lumen (in the case exemplified above, the LAA) and the position of the implant is then checked using a contrast dye and x-ray imaging. Once the position is correct, the electrodes of the implant are actuated to perform a tissue ablation or tissue sensing procedure. Tissue ablation may be performed first, using non-thermal pulsed field ablation, and then the electrodes may be employed in a sensing mode to determine an electrical parameter of the tissue such as electrical impedance which can be correlated with electrical isolation of the tissue. Once the treatment or diagnosis is completed, the catheter is detached from the implant by rotating the catheter relative to the implant to unscrew the catheter. During this process, neither the implant nor the first and second connectors rotate and the axial movement of the catheter relative to the implant causes the first and second connectors to decouple. During rotation of the catheter relative to the first electrical connector, the conducting wires will unwind from the distal end of the catheter. Once detached and electrically decoupled, the catheter is withdrawn transluminally leaving the implant in-situ in the body lumen. The catheter may be re-attached to the implant subsequently and radially retracted and withdrawn transluminally.

The system of the invention may be employed to deliver a detachable implant to a target location in the body, supply electrical energy to the implant which it is still attached to the catheter, and then be released and electrically decoupled from the catheter. The system allows use of a catheter and implant that are configured for connection by rotation of one relative to the other (for example threaded engagement or a twist-lock connection mechanism) while allowing the user of electrical connectors that employ electrical pins and sockets configured for coupling and decoupling by axial movement of one relative to the other. The embodiments described above are for occlusion and electrical isolation of the LAA by tissue ablation electrodes forming part of the occlusion apparatus. However, the system is applicable for use with other types of implants.

EQUIVALENTS

The foregoing description details presently preferred embodiments of the present disclosure. Numerous modifications and variations in practice thereof are expected to occur to those skilled in the art upon consideration of these descriptions. Those modifications and variations are intended to be encompassed within the claims appended hereto.

The invention claimed is:

1. An implant delivery system comprising:
   an elongated catheter comprising a proximal end configured for operative coupling to an electrical supply module, a distal end with a first electrical connector and at least one first conducting wire to electrically couple the electrical supply module with the first electrical connector; and
   an implant having a proximal connecting hub configured to detachably mount to the distal end of the elongated catheter by rotation of the elongated catheter relative to the proximal connecting hub, at least one second electrical connector configured to mate with the first electrical connector, and at least one active module electrically coupled to the at least one second electrical connector through a second conducting wire,
   wherein the first electrical connector is rotatably mounted to the distal end of the elongated catheter for rotation about a longitudinal axis of the elongated catheter and the at least one second electrical connector is non-rotatably attached to the proximal connecting hub of the implant such that the elongated catheter can be rotated relative to the implant to detach the elongated catheter from the implant without rotation of the first electrical connector relative to the second electrical connector, and
   wherein the at least one first conducting wire is wound around the distal end of the elongated catheter such that when the elongated catheter is rotated relative to the proximal connecting hub, the at least one first conducting wire unwinds from the distal end of the elongated catheter.

2. The system according to claim 1, in which the elongated catheter comprises a plurality of first conducting wires electrically connected to the first electrical connector, and the implant comprises a plurality of active modules each connected to the second electrical connector by a plurality of dedicated second conducting wire, wherein the first and second electrical connectors are configured to mate to electrically connect each first conducting wire with a corresponding second conducting wire.

3. The system according to claim 1, in which the at least one active module is a tissue ablation electrode.

4. The system according to claim 1, in which the implant is a radially expansible occlusion apparatus for occluding a body lumen and is adjustable between a contracted orientation suitable for transluminal delivery and a deployed orientation configured to occlude the body lumen.

5. The system according to claim 1, in which the implant is a radially expansible occlusion apparatus configured for occluding a left atrial appendage of a heart.

6. The system according to claim 1, in which the distal end of the elongated catheter and the proximal connecting hub of the implant are threaded to provide threaded engagement between the elongated catheter and the implant.

7. The system according to claim 6, in which the distal end of the elongated catheter is externally threaded and the proximal connecting hub of the implant comprises a cylindrical annulus that is internally threaded and configured to receive the externally threaded distal end of the elongated catheter.

8. The system according to claim 1, in which the proximal connecting hub of the implant comprises an annular sidewall that defined an open proximal end and two wing elements mounted to the sidewall on opposed sides of the open proximal end of the proximal connecting hub that are configured for movement from an at rest closed configuration in which the wing elements are folded over the open proximal end of the proximal connecting hub to an open tensioned configuration.

9. The system according to claim 8, in which the implant comprises the second electrical connector attached to one or both of the wing elements.

10. The system according to claim 8, in which the first electrical connector comprises an annular ring, and in which the annular sidewall of the proximal connecting hub has a proximal wall configured to abut a distal sidewall of the annular ring, wherein the second electrical connector is disposed on the proximal wall.

11. The system according to claim 1, in which one of the first electrical connector and second electrical connector comprises a housing with one or more electrical sockets and another of the first electrical connector and second electrical connector comprises a housing with one or more electrical pins corresponding to the one or more electrical sockets.

12. The system according to claim 11, in which the housing of the electrical connector comprises an electrical pin comprising a resiliently deformable sidewall in which the electrical pin projects proud of the resiliently deformable sidewall.

13. The system according to claim 11, in which the first electrical connector comprises an annular housing rotatably mounted to the distal end of the elongated catheter having a radially inner wall, a radially outer wall, a distal sidewall and a proximal sidewall, in which the distal sidewall comprises the one or more electrical pins or the one or more electrical sockets arranged coaxially with a longitudinal axis of the elongated catheter.

14. The system according to claim 1, in which the first electrical connector comprises an annular ring, and the distal end of the elongated catheter comprises a leaf spring configured to limit movement of the annular ring proximally when the elongated catheter and implant are coupled together.

\* \* \* \* \*